N. JONES.

Improvement in Trusses.

No. 5,746. Reissued Jan. 27, 1874.

Witnesses
Chas. H. Smith.
Geo. T. Pinckney

Inventor.
Nathaniel Jones.
Lemuel M. Serrell
atty.

AM. PHOTO-LITHOGRAPHIC Co. N.Y. (OSBORNE'S PROCESS)

UNITED STATES PATENT OFFICE.

NATHANIEL JONES, OF SYRACUSE, NEW YORK.

IMPROVEMENT IN TRUSSES.

Specification forming part of Letters Patent No. 127,889, dated June 11, 1872; reissue No. 5,746, dated January 27, 1874; application filed October 29, 1873.

*To all whom it may concern:*

Be it known that I, NATHANIEL JONES, of Syracuse, in the county of Onondaga and State of New York, have invented an Improvement in Trusses; and the following is declared to be a correct description of the same.

This invention relates to a truss made of a perforated plate, upon which are adjustable pads; and the same is an improvement upon the devices patented by me December 20, 1870, and September 26, 1871.

The object of the present invention is to accommodate the varying widths of pelvis, and regulate the position of the truss-pad so as to adapt it to the hernia, and also to regulate the pressure upon the same. This truss is especially adapted to scrotal and femoral hernia.

Figure 1:
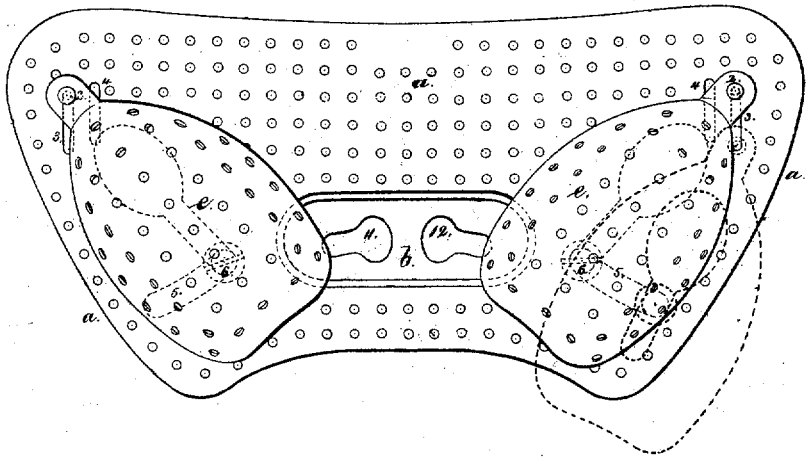
Figure 2:
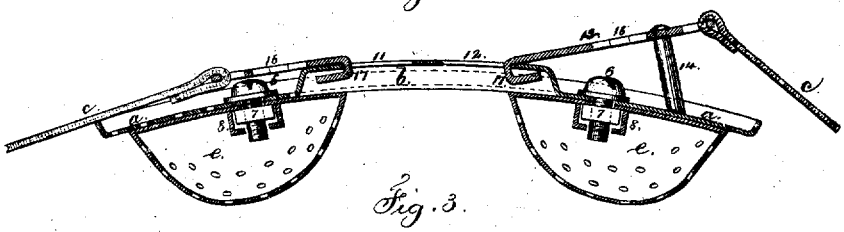
Figure 3:
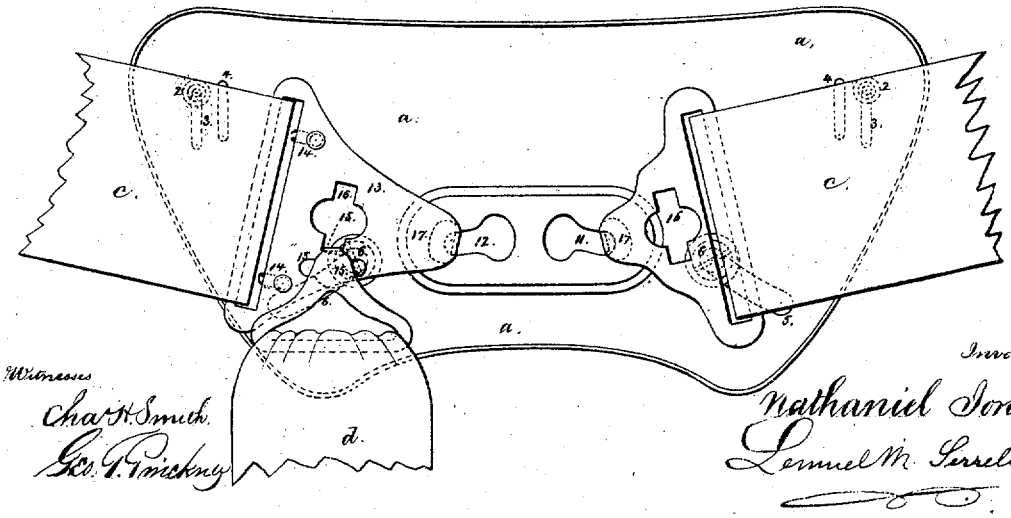

In the drawing, Figure 1 is a view of the surface of the truss-plate and pads. Fig. 2 is a horizontal section through the plate and pads; and Fig. 3 is a view of the back of the truss-plate and portions of the straps.

The truss-plate *a* is preferably made of a sheet of perforated material, with the edges turned back so as not to present a sharp edge to the surface of the body. The recessed portion *b* of this plate has holes in it for the ends of the hooks 17, by means of which the ends of the truss-strap *c* are connected. The pad *e* is made of perforated sheet metal by preference, and it is connected adjustably to the plate *a*. For this purpose the pad is made with a metallic back plate in which is a slot for the attaching-screw 6. The plate *a* is also slotted at 5 for the screw 6 to pass into a nut, 7, that is within a longitudinal and slotted case, 8, upon the back plate of the pad. The rivet or screw 2 is also shown as employed in attaching the pad, the same passing through one of the slots 3 or 4 in the plate *a*.

It will now be seen that the position of the pad can be varied by moving the same toward the center of the plate *a*, as seen in Fig. 1, or it may be moved outward, or outward and downward, as illustrated by the dotted lines in Fig. 1, and secured by the clamping-screw 6, after it has been positioned. In this manner one truss-plate is adapted to a right or left hernia, as the pad can be applied at either side and its position varied to suit the rupture; or the plate may have two pads, as shown, when the rupture is double, and those pads can be raised, lowered, or moved in or out, as required. The ends of the body-strap *c* are connected to the truss-plate *a* by hooked ends 17 entering the slots 11 and 12 in the plate *a;* but in some instances an extra pressure will be required of the plate upon the body at one or both sides. I therefore employ the lever-frame 13, with a leg or legs, 14, resting against the back of the plate *a*, so as to keep the strap *c* at a sufficient distance from the plate to cause the required pressure from the tension of the strap. The strap or straps *d* that pass between the legs have T-ended hooks 15 taking into slots 16 in the metal body of the hooks 17 or frame 13, and these slots run at right angles, or nearly so, to the T-ends of the hooks, so that it is necessary to turn the hook around before the T-head can be either entered or liberated, thus avoiding risk of the parts becoming unhooked.

I do not claim a truss-pad that is connected to the plate by slots and screws, so as to position the same as seen in Letters Patent No. 32,246. When positioned as in said patent the pad is hinged to a back plate.

I am aware that truss-plates have been employed, to which metallic springs are connected, and in some instances such springs pass more or less around the body. In my truss the straps are connected by metallic hooks at or near the center of the plate at the back thereof, so as to apply the required force to hold the plate in place and allow freedom in the movement of the body, and to the face of such truss-plate one or more hollow sheet-metal pads are connected adjustably, so as to position such pads laterally to suit the location of the rupture.

I claim as my invention—

1. In a hernial truss the combination of the following devices: First, a metallic plate to rest against the surface of the body and having the edges turned back to form flanges; second, one or more perforated metallic pads with flat or nearly flat backs attached to such plate and capable of lateral adjustment upon the same; and, third, flexible straps attached by metallic connections at the back and near the center of the metallic plate, substantially as set forth.

2. The longitudinal slotted case 8 within the pad *a* for the nut 7, in combination with the plate *a*, having slots 3 or 4 for the pin or screws 2, and slot 5 for the screw 6, substantially as set forth.

3. A truss-plate made with its edges turned with rounding flanges, and with attaching-slots in a recessed central portion of the plate, in combination with a pad that is attached to such plate, and adjustable upon the same to accommodate the position of the hernia, substantially as set forth.

4. The lever attaching-frame 13, made with the leg or legs 14, and applied between the truss-plate *a* and strap *c*, substantially as and for the purpose set forth.

Signed by me this 24th day of October, A. D. 1873.

NATHANIEL JONES.

Witnesses:
GEO. T. PINCKNEY,
CHAS. H. SMITH.